United States Patent
Zhuo et al.

(10) Patent No.: US 9,988,387 B2
(45) Date of Patent: *Jun. 5, 2018

(54) IMIDAZO[1,2-B][1,2,4]TRIAZINES AS C-MET INHIBITORS

(71) Applicants: Incyte Holdings Corporation, Wilmington, DE (US); Incyte Corporation, Wilmington, DE (US)

(72) Inventors: Jincong Zhuo, Garnet Valley, PA (US); Chunhong He, Chadds Ford, PA (US); Wenqing Yao, Chadds Ford, PA (US)

(73) Assignees: Incyte Holdings Corporation, Wilmington, DE (US); Incyte Corporation, Wilmington, DE (US)

(*) Notice: Subject to any disclaimer, the term of this patent is extended or adjusted under 35 U.S.C. 154(b) by 0 days. days.

This patent is subject to a terminal disclaimer.

(21) Appl. No.: 14/918,879

(22) Filed: Oct. 21, 2015

(65) Prior Publication Data

US 2016/0137650 A1 May 19, 2016

Related U.S. Application Data

(63) Continuation of application No. 13/915,702, filed on Jun. 12, 2013, now Pat. No. 9,221,824, which is a continuation of application No. 13/019,718, filed on Feb. 2, 2011, now Pat. No. 8,487,096.

(60) Provisional application No. 61/300,946, filed on Feb. 3, 2010.

(51) Int. Cl.
- C07D 487/04 (2006.01)
- C07D 403/04 (2006.01)
- A61K 31/53 (2006.01)
- A61P 35/00 (2006.01)

(52) U.S. Cl.
CPC ............ *C07D 487/04* (2013.01); *A61K 31/53* (2013.01); *C07D 403/04* (2013.01)

(58) Field of Classification Search
CPC ............... C07D 487/04; C07D 403/04; A61K 31/4709; A61K 31/4245; A61K 31/4708
USPC .......................................... 544/184; 514/243
See application file for complete search history.

(56) References Cited

U.S. PATENT DOCUMENTS

| | | | |
|---|---|---|---|
| 2,837,520 A | 6/1958 | Fusco et al. | |
| 4,209,621 A | 6/1980 | Dusza et al. | |
| 4,405,619 A | 9/1983 | Heilman et al. | |
| 5,236,917 A | 8/1993 | Dunlap et al. | |
| 5,254,548 A | 10/1993 | Wermuth et al. | |
| 7,005,431 B2 | 2/2006 | Bettati et al. | |
| 7,176,203 B2 | 2/2007 | Chambers et al. | |
| 7,683,060 B2 | 3/2010 | Zhuo et al. | |
| 7,767,675 B2 | 8/2010 | Zhuo | |
| 8,420,645 B2 | 4/2013 | Weng et al. | |
| 8,461,330 B2 | 6/2013 | Zhuo et al. | |
| 8,487,096 B2 | 7/2013 | Zhuo et al. | |
| 8,901,123 B2 | 12/2014 | Weng et al. | |
| 9,221,824 B2* | 12/2015 | Zhuo | A61K 31/53 |
| 2005/0075340 A1 | 4/2005 | Zhang et al. | |
| 2005/0085473 A1 | 4/2005 | Van Hirschheydt et al. | |
| 2005/0165023 A1 | 7/2005 | Bettati et al. | |
| 2005/0261297 A1 | 11/2005 | Igarashi et al. | |
| 2006/0046991 A1 | 3/2006 | Cui et al. | |
| 2006/0058303 A1 | 3/2006 | Chambers et al. | |
| 2007/0191376 A1 | 8/2007 | Zou et al. | |
| 2008/0039457 A1 | 2/2008 | Zhuo et al. | |
| 2008/0167287 A1 | 7/2008 | Zhuo et al. | |
| 2009/0124609 A1 | 5/2009 | Albrecht et al. | |
| 2009/0124612 A1 | 5/2009 | Albrecht et al. | |
| 2009/0291956 A1 | 11/2009 | Weng et al. | |
| 2011/0136781 A1 | 6/2011 | Zhuo et al. | |
| 2013/0289036 A1 | 10/2013 | Weng et al. | |
| 2013/0324515 A1 | 12/2013 | Zhuo et al. | |
| 2015/0148348 A1 | 5/2015 | Weng et al. | |

FOREIGN PATENT DOCUMENTS

| | | |
|---|---|---|
| CA | 1246568 A | 12/1988 |
| CA | 2158994 A1 | 9/1994 |
| EP | 0 430 385 A2 | 6/1991 |
| EP | 0 443 453 A1 | 8/1991 |
| EP | 1 640 010 A1 | 3/2006 |
| FR | 2662163 A1 | 11/1991 |
| JP | S63-037347 A | 2/1988 |
| JP | S63-199347 A | 8/1988 |
| JP | S63-310891 A | 12/1988 |
| JP | H03-013934 A | 1/1991 |
| JP | H04-251243 A | 9/1992 |
| JP | H05-232618 A | 9/1993 |
| JP | 2001-043978 A | 2/2001 |
| WO | 1983/000864 A1 | 3/1983 |
| WO | 1999/006404 A1 | 2/1999 |
| WO | 2001/034603 A2 | 5/2001 |

(Continued)

OTHER PUBLICATIONS

Abdel-Rahman et al. (1993) "Synthesis of some new thioethers of 1,2,4-triazine-3-hydrazones and assays for their anticancer and antihuman immune virus activities," Farmaco. 48(3):397-406.

Acero-Alarcon et al. (1999) "UUnusual Ring Closure Reaction of Amides with Pyrimidines: Novel Stereoselective Synthesis of Hexahydroimidazo[1,2-c]pyrimidines," Synthesis. 12:2124-2130.

Balkovetz et al. (1999) "Hepatocyte Growth Factor and the Kidney: It is Not Just for the Liver." Intl. Rev. Cytol. 186:225-250.

Bennet et al.: Eds. (1996) Cecil Textbook of Medicine. 20th Ed. vol. 1. pp. 1004-1010.

(Continued)

*Primary Examiner* — Venkataraman Balasubramanian
(74) *Attorney, Agent, or Firm* — Lathrop Gage LLP

(57) ABSTRACT

The present invention relates to imidazo[1,2-b][1,2,4]triazines that are inhibitors of c-Met and are useful in the treatment of c-Met associated diseases including cancer.

12 Claims, No Drawings

(56) References Cited

FOREIGN PATENT DOCUMENTS

| | | | |
|---|---|---|---|
| WO | 2001/034605 A1 | 5/2001 |
| WO | 2002/072579 A1 | 9/2002 |
| WO | 2002/079203 A1 | 10/2002 |
| WO | 2003/080621 A1 | 10/2003 |
| WO | 2003/087026 A1 | 10/2003 |
| WO | 2003/097641 A2 | 11/2003 |
| WO | 2004/005290 A1 | 1/2004 |
| WO | 2004/005291 A1 | 1/2004 |
| WO | 2004/020438 A2 | 3/2004 |
| WO | 2004/058769 A2 | 7/2004 |
| WO | 2004/076412 A2 | 9/2004 |
| WO | 2005/004607 A1 | 1/2005 |
| WO | 2005/004808 A2 | 1/2005 |
| WO | 2005/005378 A2 | 1/2005 |
| WO | 2005/010005 A1 | 2/2005 |
| WO | 2005/014598 A1 | 2/2005 |
| WO | 2005/028475 A2 | 3/2005 |
| WO | 2005/030140 A2 | 4/2005 |
| WO | 2005/040345 A2 | 5/2005 |
| WO | 2005/039586 A1 | 6/2005 |
| WO | 2005/040154 A1 | 6/2005 |
| WO | 2005/070891 A2 | 8/2005 |
| WO | 2005/073224 A2 | 8/2005 |
| WO | 2005/077953 A1 | 8/2005 |
| WO | 2005/097800 A1 | 10/2005 |
| WO | 2005/113494 A2 | 12/2005 |
| WO | 2005/121125 A1 | 12/2005 |
| WO | 2006/014325 A2 | 2/2006 |
| WO | 2006/124354 A2 | 11/2006 |
| WO | 2007/013673 A1 | 2/2007 |
| WO | 2007/015866 A2 | 2/2007 |
| WO | 2007/025090 A2 | 3/2007 |
| WO | 2007/064797 A2 | 6/2007 |
| WO | 2007/075567 A1 | 7/2007 |
| WO | 2007/096764 A2 | 8/2007 |
| WO | 2008/008539 A2 | 1/2008 |
| WO | 2008/051805 A2 | 5/2008 |
| WO | 2008/058126 A2 | 5/2008 |
| WO | 2008/064157 A1 | 5/2008 |
| WO | 2008/144767 A1 | 11/2008 |
| WO | 2009/091374 A2 | 7/2009 |
| WO | 2009/143211 A2 | 11/2009 |

OTHER PUBLICATIONS

Berge et al. (1977) "Pharmaceutical salts," Journal of Pharmaceutical Sciences. 66(1):1-19.

Birchmeier et al. (2003) "Met, Metastasis, Motility, and More," Nature. 4:915-925.

Blom et al. (2004) "Preparative LC-MS Purification: Improved Compound-Specific Method Optimization," J. Comb. Chem. 6:874-883.

Blume-Jensen et al. (2001) "Oncogenic kinase signaling," Nature. 411:355-365.

Boccaccio et al. (2006) "Invasive growth: a MET-driven genetic programme for cancer and stem cells," Nature. 6:637-645.

Bolen (1993) "Nonreceptor tyrosine protein kinases," Oncogene. 8(8):2025-2031.

Brittain (1999) "Methods for the Characterization of Polymorphs and Solvates," In; Ch. 6; Polymorphism in Pharmaceutical Solids. vol. 95. Marcel Dekker, Inc. New York, New York. pp. 227-278.

Calic et al. (2005) "Flavonoids as Inhibitors of Lck and Fyn Kinases," Croatica Chemical Acta. 78(3):367-374.

Christiansen et al. (2005) "c-Met as a target for human cancer and characterization of inhibitors for therapeutic Intervention," Cancer Letters. 225:1-26.

Cohen et al. (1999) "Current Opinion in Chemical Biology," 3:459-465.

Corso et al. (2005) "Cancer therapy: can the challenge be MET?" Trends in Molecular Medicine. 11(6):284-292.

Crestani et al. (2002) "Differential Role of Neutrophils and Aveolar Macrophages in Hepatocyte Growth Factor Production in Pulmonary Fibrosis," Laboratory Investigation. 82(8):1015-1022.

Dermer et al. (1994) "Another Anniversary for the War on Cancer," Bio/Technology. 12:320.

Druzhinin et al. (1993) "Acid-base Reactions of Imidazo[1,2-131-1,2,4-Triazines (Imitrines) with Proton Donors," Russian Journal of General Chemistry. 63(6):953-958.

Eguchi et al. (1999) "Changes in liver regenerative factors in a case of living-related liver transplantationm," Clinical Transplantation. 15:536-544.

Fabbro et al. (2002) "Protein kinases as targets for anticancer agents: from inhibitors to useful drugs," Pharmacology & Therapeutics. 93:79-98.

Freshney et al. (1983) Culture of Animal Cells, A Manual of Basic Technique. Alan R. Liss, Inc. New York, New York. p. 4.

Fusco et al. (1955) "Ricerche Suite Triazine Assimetriche Sintesi Di Derivati Tetraziandenici," Rendiconti. 88:194-202.—English translation.

Gennaro: Ed. (1985) Remington's Pharmaceutical Sciences. 17th Ed. Mack Publishing Company. Easton, Pennsylvania. p. 1418.

Golub et al. (1999) "Molecular Classification of Cancer: Class Discovery and Class Prediction by Gene Expression Monitoring," Science. 286:531-537.

Greene et al. (1991) Protective Groups in Organic Synthesis. 2nd. Ed. Wiley & Sons.

Higuchi et al. (1987) "Pro-drugs as Novel Delivery Systems," vol. 14 of the A.C.S. Symposium Series Bioreversible Carriers in Drug Design. Ed.: Edward B. Roche. American Pharmaceutical Association and Pereamon Press.

Holla et al. (2003) "Synthesis and reactions of new Nbridged heterocycles derived from 3-substituted-4,5-diamino-1,2,4-triazoles," Indian Journal of Chemistry, Section B: Organic Chemistry Including Medicinal Chemistry. 42B(9)2054-2058.

Koblish et al. (2008) "Preclinical in vivo characteristic of INCB028060, a novel, potent and highly selective c-Met inhibitor," J. Clinical Oncology. 26(15S):14561.

Koch et al. (1996) "Hepatocyte Growth Factor," Arthritis and Rheumatism. 39(9):1566-1575.

Krayushkin et al. (2005) "Synthesis and Structure of 5-Indoly1-6-thieny1-1,2,4-Triazines," Russian Journal of Organic Chemistry. 41(6):875-883.

Kruglenko et al. (1998) "Condensed Imidazo-1,2,4-azines. 28. Synthesis and Transformations of 2-Aroylmethy1-6,7-Diphenylimidazo-[1,2-b]-1,2,4-Triazin-4H-3-Ones," Chemistry of Heterocyclic Compounds. 34(2):232-236.

Labouta et al. (1987) "Potential Antineoplastics: Some Substituted Imidazo[1,2-141,2,4]triazines,[4,3-b][1,2,4]triazines and imidazotriazino-[5,6-b]indoles," Journal of the Serbian Chemical Society. 52(9):523-527.

Labouta et al. (1988) "Synthesis of some substituted triazolo[4,3-b][1,2,4]triazines as potential anticancer agents," Monatshefte fuer Chemie. 119(5):591-596.

Liu (2002) "Hepatocyte growth factor and the kidney," Current Opinion in Nephrology and Hypertension. 11:23-30.

Liu (2008) "Discovery and Characterization of INCB028060: A Novel, Potent and Selective MET RTK Inhibitor for Cancer Treatment," In; The AACR Annual Meeting, Apr. 12-16, 2008.

Liu (2008) "INCB28060 A Novel, Potent and Selective c-MET RTK Inhibitor for Cancer Treatment" In; GTC Bio: The 4th Modern Drug Discovery & Development Summit, Oct. 15-17, 2008. San Diego, California.

Ju (2008) "Targeting the c-Met signaling pathway for cancer treatment," Expert Opin. Investig. Drugs. 17(7):997-1011.

Ma et al. (2002) "Hepatocyte growth factor is a survival factor for endothelial cells and is expressed in human atherosclerotic plaques," Atherosclerosis. 164:79-87.

Madhusudan et al. (2004) "Tyrosine kinase inhibitors in cancer therapy," Clinical Biochemistry. 37:618-635.

Manning et al. (2002) "The Protein Kinase Complement of the Human Genome," Science. vol. 298. pp. 1912-1916, 1933-1934.

Mass (2004) "The HER receptor family: a rich target for therapeutic development," Int. J. Radiation Oncology Bio. Phys. 58(3):932-940.

(56) References Cited

OTHER PUBLICATIONS

Matsumoto et al. (2001) "Hepatocyte growth factor: Renotropic role and potential therapeutics for renal diseases," Kidney International. 59:2023-2038.
Miyazawa et al. (1998) "Protection of Hippocampal Neurons from Ischemia-induced Delayed Neuronal Death by Hepatocyte Growth Factor: A Novel Neurotrophic Factor," Journal of Cerebral Blood Flow and Metabolism. 18:345-348.
Morishita et al. (2002) "Hepatocyte Growth Factor as Cardiovascular Hormone: Role of HGF in the Pathogenesis of Cardiovascular Disease," Endocrine Journal. 49(3):273-284.
Morishita et al. (2004) "Therapeutic Angiogenesis using Hepatocyte Growth Factor (HGF)," Current Gene Therapy. 4:199-206.
Povstyanoi et al. (1984) Izvestiya Timiryazevskoi Sel'skokhozyaistvennoi Akademii 5:155-159.—CAPLUS Abstract provided.
Rossi et al. (1958) "Pigmenti Fluorescenti derivati dall'1,4,7,9—tetraziandene," La Chimica E L 'Industria. 40 (10):827-830.
Segura-Flores et al. (2004) "Factor de crecimiento de hepatocitos (HGF) y sus aplicaciones terapeuticas," Revista de Gastroenterologia de Mexico. 69(4):243-250.
STN search dated Oct. 16, 2006.
STN search report (Registry file compounds, dated Jul. 26, 2006).
STN search report (Registry file compounds, dated Nov. 1, 2006).
STN search report (Registry file compounds, dated Oct. 19, 2006).
Tomchin (1982) "Heterocyclic semicarbazones and thiosemicarbazones. XLV. 1,2,4-Triazinoindole derivatives with a condensed imidazole, thiazole or triazole ring," Journal of Organic Chemistry of the USSR. 18(6):1103-1110.
Vidal et al. (2000) "Effect of imidazo[1,2-a]pyrimidine derivatives on leukocyte function," Inflammation Research. 50:317-320.
Wang et al. (2003) "Potent and selective inhibitors of the Met [hepatocyte growth factor/scatter factor (HGF/SF) receptor] tyrosine kinase block HGF/SF-induced tumor cell growth and invasion," Molecular Cancer Therapeutics. 2:1085-1092.
Wermuth (1996) "Molecular Variations Based on Isosteric Replacements," In; The Practice of Medical Chemistry. pp. 203-237.
International Preliminary Report on Patentability corresponding to International Patent Application No. PCT/US2007/085100, dated Jun. 4, 2009.
International Preliminary Report on Patentability corresponding to International Patent Application No. PCT/US2009/044622, dated Nov. 23, 2010.
International Preliminary Report on Patentability corresponding to International Patent Application No. PCT/US2007/075254, dated Feb. 10, 2009.
International Search Report corresponding to International Patent Application No. PCT/US2007/075254, dated Jan. 18, 2008.
International Search Report corresponding to International Patent Application No. PCT/US2007/085100, dated Apr. 11, 2008.
International Search Report with Written Opinion corresponding to International Patent Application No. PCT/US2011/023464, dated Apr. 7, 2011.
U.S. Appl. No. 11/942,130, filed Nov. 19, 2007, 2008/0167287, Jul. 10, 2008, U.S. Pat. No. 7,767,675, Aug. 3, 2010, Jincong Zhuo.
U.S. Appl. No. 12/813,148, filed Jun. 10, 2010, 2011/0136781, Jun. 9, 2011, U.S. Pat. No. 8,461,330, Jun. 11, 2013, Jincong Zhuo.
U.S. Appl. No. 13/895,799, filed May 16, 2013, 2013/0324515, Dec. 5, 2013, Jincong Zhuo.
U.S. Appl. No. 15/016,841, filed Feb. 5, 2016, Jincong Zhuo.
U.S. Appl. No. 12/469,360, filed May 20, 2009, 2009/0291956, Nov. 26, 2009, U.S. Pat. No. 8,420,645, Apr. 16, 2013, Lingkai Weng.
U.S. Appl. No. 13/793,864, filed Mar. 11, 2013, 2013/0289036, Oct. 31, 2013, U.S. Pat. No. 8,901,123, Dec. 2, 2014, Lingkai Weng.
U.S. Appl. No. 14/525,381, filed Oct. 28, 2014, 2015/0148348, May 28, 2015, Lingkai Weng.
U.S. Appl. No. 13/019,718, filed Feb. 2, 2011, 2011/0212967, Sep. 1, 2011, U.S. Pat. No. 8,487,096, Jul. 16, 2013, Jincong Zhuo.
U.S. Appl. No. 13/915,702, filed Jun. 12, 2013, 2013/0345224, Dec. 26, 2013, U.S. Pat. No. 9,221,824, Dec. 29, 2015, Jincong Zhuo.

\* cited by examiner ism IMIDAZO[1,2-B][1,2,4]TRIAZINES AS C-MET INHIBITORS

RELATED APPLICATION

This application is a continuation of U.S. application Ser. No. 13/915,702, filed Jun. 12, 2013, which is a continuation of U.S. application Ser. No. 13/019,718, filed Feb. 2, 2011, now issued as U.S. Pat. No. 8,487,096, which claims priority to U.S. Provisional Application No. 61/300,946, filed Feb. 3, 2010, titled "IMIDAZO[1,2-b][1,2,4]TRIAZINES AS C-MET INHIBITORS." The contents of any patents, patent applications, and references cited throughout this specification are hereby incorporated by reference in their entireties.

FIELD OF THE INVENTION

The present invention relates to imidazo[1,2-b][1,2,4] triazines that are inhibitors of c-Met and are useful in the treatment of c-Met associated diseases including cancer.

BACKGROUND OF THE INVENTION

Protein kinases (PKs) are a group of enzymes that regulate diverse, important biological processes including cell growth, survival and differentiation, organ formation and morphogenesis, neovascularization, tissue repair and regeneration, among others. Protein kinases exert their physiological functions through catalyzing the phosphorylation of proteins (or substrates) and thereby modulating the cellular activities of the substrates in various biological contexts. In addition to the functions in normal tissues/organs, many protein kinases also play more specialized roles in a host of human diseases including cancer. A subset of protein kinases (also referred to as oncogenic protein kinases), when dysregulated, can cause tumor formation and growth, and further contribute to tumor maintenance and progression (Blume-Jensen P et al, Nature 2001, 411(6835):355-365). Thus far, oncogenic protein kinases represent one of the largest and most attractive groups of protein targets for cancer intervention and drug development.

c-Met, a proto-oncogene, is a member of a distinct subfamily of heterodimeric receptor tyrosine kinases which include Met, Ron, and Sea (Birchmeier, C. et al., Nat. Rev. Mol. Cell Biol. 2003, 4(12):915-925; Christensen, J. G. et al., Cancer Lett. 2005, 225(1):1-26). The only high affinity ligand for c-Met is the hepatocyte growth factor (HGF), also known as scatter factor (SF). Binding of HGF to c-Met induces activation of the receptor via autophosphorylation resulting in an increase of receptor dependent signaling. Both c-Met and HGF are widely expressed in a variety of organs, but their expression is normally confined to the cells of epithelial and mesenchymal origin, respectively. The biological functions of c-Met (or c-Met signaling pathway) in normal tissues and human malignancies such as cancer have been well documented (Christensen, J. G. et al., Cancer Lett. 2005, 225(1):1-26; Corso, S. et al., Trends in Mol. Med. 2005, 11(6):284-292).

HGF and c-Met are each required for normal mammalian development, and abnormalities reported in both HGF- and c-Met-null mice are consistent with proximity of embryonic expression and epithelial-mesenchymal transition defects during organ morphogenesis (Christensen, J. G. et al., Cancer Lett. 2005, 225(1):1-26). Consistent with these findings, the transduction of signaling and subsequent biological effects of HGF/c-Met pathway have been shown to be important for epithelial-mesenchymal interaction and regulation of cell migration, invasion, cell proliferation and survival, angiogenesis, morphogenesis and organization of three-dimensional tubular structures (e.g. renal tubular cells, gland formation) during development. The specific consequences of c-Met pathway activation in a given cell/tissue are highly context-dependent.

Dysregulated c-Met pathway plays important and sometimes causative (in the case of genetic alterations) roles in tumor formation, growth, maintenance and progression (Birchmeier, C. et al., Nat. Rev. Mol. Cell. Biol. 2003, 4(12):915-925; Boccaccio, C. et al., Nat. Rev. Cancer 2006, 6(8):637-645; Christensen, J. G. et al., Cancer Lett. 2005, 225(1): 1-26). HGF and/or c-Met are overexpressed in significant portions of most human cancers, and are often associated with poor clinical outcomes such as more aggressive disease, disease progression, tumor metastasis and shortened patient survival. Further, patients with high levels of HGF/c-Met proteins are more resistant to chemotherapy and radiotherapy. In addition to the abnormal HGF/c-Met expression, the c-Met receptor can also be activated in cancer patients through genetic mutations (both germline and somatic) and gene amplification. Although gene amplification and mutations are the most common genetic alterations that have been reported in patients, the receptor can also be activated by deletions, truncations, gene rearrangement, as well as abnormal receptor processing and defective negative regulatory mechanisms.

The various cancers in which c-Met is implicated include, but are not limited to: carcinomas (e.g., bladder, breast, cervical, cholangiocarcinoma, colorectal, esophageal, gastric, head and neck, kidney, liver, lung, nasopharygeal, ovarian, pancreas, prostate, thyroid); musculoskeletal sarcomas (e.g., osteosarcaoma, synovial sarcoma, rhabdomyosarcoma); soft tissue sarcomas (e.g., MFH/fibrosarcoma, leiomyosarcoma, Kaposi's sarcoma); hematopoietic malignancies (e.g., multiple myeloma, lymphomas, adult T cell leukemia, acute myelogenous leukemia, chronic myeloid leukemia); and other neoplasms (e.g., glioblastomas, astrocytomas, melanoma, mesothelioma and Wilm's tumor (www.vai.org/met/; Christensen, J. G. et al., Cancer Lett. 2005, 225(1):1-26).

The notion that the activated c-Met pathway contributes to tumor formation and progression and could be a good target for effective cancer intervention has been further solidified by numerous preclinical studies (Birchmeier, C. et al., Nat. Rev. Mol. Cell Biol. 2003, 4(12):915-925; Christensen, J. G. et al., Cancer Lett. 2005, 225(1):1-26; Corso, S. et al., Trends in Mol. Med. 2005, 11(6):284-292). For example, studies showed that the tpr-met fusion gene, overexpression of c-met and activated c-met mutations all caused oncogenic transformation of various model cell lines and resulted in tumor formation and metastasis in mice. More importantly, significant anti-tumor (sometimes tumor regression) and anti-metastasis activities have been demonstrated in vitro and in vivo with agents that specifically impair and/or block HGF/c-Met signaling. Those agents include anti-HGF and anti-c-Met antibodies, HGF peptide antagonists, decoy c-Met receptor, c-Met peptide antagonists, dominant negative c-Met mutations, c-Met specific antisense oligonucleotides and ribozymes, and selective small molecule c-Met kinase inhibitors (Christensen, J. G. et al., Cancer Lett. 2005, 225(1):1-26).

In addition to the established role in cancer, abnormal HGF/c-Met signaling is also implicated in atherosclerosis, lung fibrosis, renal fibrosis and regeneration, liver diseases, allergic disorders, inflammatory and autoimmune disorders, cerebrovascular diseases, cardiovascular diseases, conditions associated with organ transplantation (Ma, H. et al., Atherosclerosis. 2002, 164(1):79-87; Crestani, B. et al., Lab. Invest. 2002, 82(8):1015-1022; Sequra-Flores, A. A. et al., Rev. Gastroenterol. Mex. 2004, 69(4)243-250; Morishita, R. et al., Curr. Gene Ther. 2004, 4(2)199-206; Morishita, R. et al., Endocr. J. 2002, 49(3)273-284; Liu, Y., Curr. Opin. Nephrol. Hypertens. 2002, 11(1):23-30; Matsumoto, K. et al., Kidney Int. 2001, 59(6):2023-2038; Balkovetz, D. F. et al., Int. Rev. Cytol. 1999, 186:225-250; Miyazawa, T. et al., J. Cereb. Blood Flow Metab. 1998, 18(4)345-348; Koch, A. E. et al., Arthritis Rheum. 1996, 39(9):1566-1575; Futamatsu, H. et al., Circ. Res. 2005, 96(8)823-830; Eguchi, S. et al., Clin. Transplant. 1999, 13(6)536-544).

New or improved forms of existing agents which inhibit kinases such as c-Met are continually needed for developing more effective pharmaceuticals to treat cancer and other diseases. The compounds and salts described herein are directed toward these needs and other ends.

SUMMARY OF THE INVENTION

The present invention provides, inter alia, the following compounds which are c-Met inhibitors:
2-fluoro-N-[(2R)-2-hydroxypropyl]-4-[7-(quinolin-6-ylmethyl)imidazo[1,2-b][1,2,4]triazin-2-yl]benzamide (Formula I);
2-chloro-N-methyl-4-(7-(quinolin-6-ylmethyl)imidazo[1,2-b][1,2,4]triazin-2-yl)benzamide (Formula II);
2-chloro-N-[(1S)-1-(5-methyl-1,2,4-oxadiazol-3-yl)ethyl]-4-[7-(quinolin-6-ylmethyl)imidazo[1,2-b][1,2,4]triazin-2-yl]benzamide (Formula III);
N-methyl-5-[7-(quinolin-6-ylmethyl)imidazo[1,2-b][1,2,4]triazin-2-yl]pyridine-2-carboxamide (Formula IV); and
N,2-dimethyl-4-[7-(quinolin-6-ylmethyl)imidazo[1,2-b][1,2,4]triazin-2-yl]benzamide (Formula V).

The present invention further provides a pharmaceutically acceptable salt of any one of the aforementioned compounds.

The present invention further provides a method of inhibiting activity of c-Met kinase comprising contacting the kinase with a compound or salt of the invention.

The present invention further provides a method of inhibiting the HGF/c-Met kinase signaling pathway in a cell comprising contacting the cell with a compound or salt of the invention.

The present invention further provides a method of inhibiting the proliferative activity of a cell comprising contacting the cell with a compound or salt of the invention.

The present invention further provides a method of inhibiting tumor growth in a patient comprising administering to the patient a therapeutically effective amount of a compound or salt of the invention.

The present invention further provides a method of inhibiting tumor metastasis in a patient comprising administering to the patient a therapeutically effective amount of a compound or salt of the invention.

The present invention further provides a method of treating a disease in a patient, wherein the disease is associated with dysregulation of the HGF/c-MET signaling pathway, comprising administering to the patient a therapeutically effective amount of a compound or salt of the invention.

The present invention further provides a method of treating cancer in a patient comprising administering to the patient a therapeutically effective amount of a compound or salt of the invention.

The present invention provides a compound of the invention for use in therapy.

The present invention provides the use of a compound of the invention for the preparation of a medicament for use in therapy. In one embodiment, the present invention provides the use of any one of compounds of Formula I, II, III, IV, or V for the preparation of a medicament for use in treatment of cancer.

DETAILED DESCRIPTION

The present invention provides, inter alia, the following compounds which are c-Met inhibitors:
2-fluoro-N-[(2R)-2-hydroxypropyl]-4-[7-(quinolin-6-ylmethyl)imidazo[1,2-b][1,2,4]triazin-2-yl]benzamide (Formula I);
2-chloro-N-methyl-4-(7-(quinolin-6-ylmethyl)imidazo[1,2-b][1,2,4]triazin-2-yl)benzamide (Formula II);
2-chloro-N-[(1S)-1-(5-methyl-1,2,4-oxadiazol-3-yl)ethyl]-4-[7-(quinolin-6-ylmethyl)imidazo[1,2-b][1,2,4]triazin-2-yl]benzamide (Formula III);
N-methyl-5-[7-(quinolin-6-ylmethyl)imidazo[1,2-b][1,2,4]triazin-2-yl]pyridine-2-carboxamide (Formula IV); and
N,2-dimethyl-4-[7-(quinolin-6-ylmethyl)imidazo[1,2-b][1,2,4]triazin-2-yl]benzamide (Formula V).

Formula I

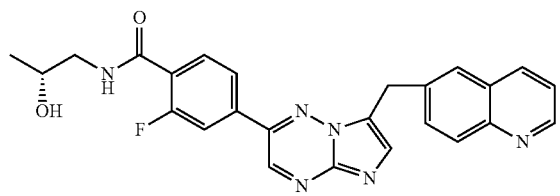 [SMILES: C[C@@H](O)CNC(=O)c1ccc(-c2cnc3ncc(Cc4ccc5ncccc5c4)n3n2)cc1F]

Formula II

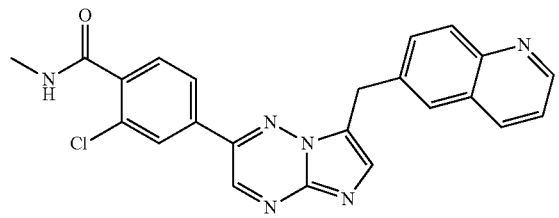

Formula III

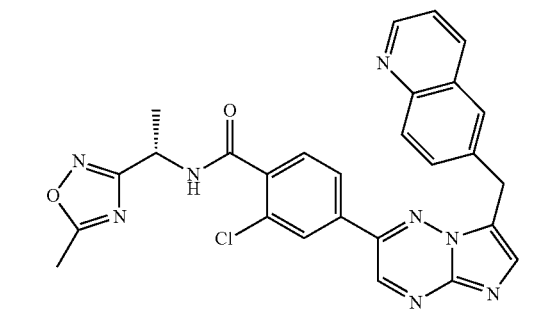

Formula IV

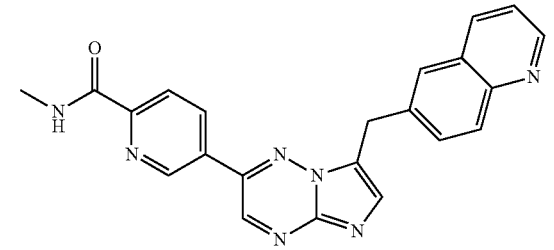

Formula V

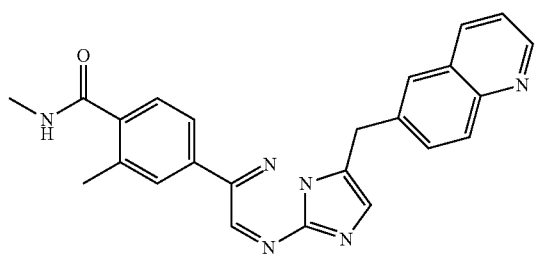

Here and elsewhere, where discrepancies exist between a compound's name and a compound's structure, the chemical structure will control.

The present invention further provides pharmaceutically acceptable salts of any of the aforementioned compounds.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention also include all isotopes of atoms occurring in the intermediates or final compounds. Isotopes include those atoms having the same atomic number but different mass numbers. For example, isotopes of hydrogen include tritium and deuterium.

In some embodiments, the compounds of the invention, or their salts, are substantially isolated. By "substantially isolated" is meant that the compound or salt is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17$^{th}$ ed., Mack Publishing Company, Easton, Pa., 1985, p. 1418 and *Journal of Pharmaceutical Science,* 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Methods of Use

The compounds of the present invention can act as inhibitors of c-Met. Treatment of a cell (in vitro or in vivo) that expresses c-Met with a compound of the invention can result in inhibiting the ligand/kinase signaling pathway and inhibiting downstream events related to the signaling pathway such as cellular proliferation and increased cell motility. For example, the compounds of the invention can block and/or impair the biochemical and biological processes resulting from c-Met pathway activation, including, but not limited to, c-Met kinase activation (e.g. c-Met phosphorylation) and signaling (activation and recruitment of cellular substrates such as Gab1, Grb2, Shc and c-Cbl and subsequent activation of a number of signal transducers including PI-3 kinase, PLC-γ, STATs, ERK1/2 and FAK), cell proliferation and survival, cell motility, migration and invasion, metastasis, angiogenesis, and the like. Thus, the present invention further provides methods of inhibiting a ligand/kinase signaling pathway such as the HGF/c-Met kinase signaling pathway in a cell by contacting the cell with a compound of the invention. The present invention further provides methods of inhibiting proliferative activity of a cell or inhibiting cell motility by contacting the cell with a compound of the invention.

The present invention further provides methods of treating diseases associated with a dysregulated c-Met kinase signaling pathway, including abnormal activity and/or overexpression of the c-Met, in an individual (e.g., patient) by administering to the individual in need of such treatment a therapeutically effective amount or dose of a compound of the present invention or a pharmaceutical composition thereof. In some embodiments, the dysregulated kinase is overexpressed in the diseased tissue of the patient. In some embodiments, the dysregulated kinase is abnormally active in the diseased tissue of the patient. Dysregulation of c-Met and the HGF/c-Met signaling pathway is meant to include activation of the enzyme through various mechanisms including, but not limited to, HGF-dependent autocrine and paracrine activation, c-met gene overexpression and amplification, point mutations, deletions, truncations, rearrangement, as well as abnormal c-Met receptor processing and defective negative regulatory mechanisms.

In some embodiments, the compounds of the invention are useful in treating diseases such as cancer, atherosclerosis, lung fibrosis, renal fibrosis and regeneration, liver disease, allergic disorder, inflammatory disease, autoimmune disorder, cerebrovascular disease, cardiovascular disease, or condition associated with organ transplantation. In further embodiments, the compounds of the invention can be useful in methods of inhibiting tumor growth or metastasis of a tumor in a patient.

Example cancers treatable by the methods herein include bladder cancer, breast cancer, cervical cancer, cholangiocarcinoma cancer, colorectal cancer, esophageal cancer, gastric cancer, head and neck cancer, cancer of the kidney, liver cancer, lung cancer, nasopharygeal cancer, ovarian cancer, pancreatic cancer, prostate cancer, thyroid cancer, osteosarcoma, synovial sarcoma, rhabdomyosarcoma, MFH/fibrosarcoma, leiomyosarcoma, Kaposi's sarcoma, multiple myeloma, lymphoma, adult T cell leukemia, acute myelogenous leukemia, chronic myeloid leukemia, glioblastoma, astrocytoma, melanoma, mesothelioma, or Wilm's tumor, and the like.

Thus, in one embodiment, provided herein is a method of treating cancer in a subject, comprising administering to the subject 2-fluoro-N-[(2R)-2-hydroxypropyl]-4-[7-(quinolin-6-ylmethyl)imidazo[1,2-b][1,2,4]triazin-2-yl]benzamide, or a pharmaceutically acceptable salt thereof, such that the cancer is treated.

In another embodiment, provided herein is a method of treating cancer in a subject, comprising administering to the subject 2-chloro-N-methyl-4-(7-(quinolin-6-ylmethyl)imidazo[1,2-b][1,2,4]triazin-2-yl)benzamide, or a pharmaceutically acceptable salt thereof, such that the cancer is treated.

In another embodiment, provided herein is a method of treating cancer in a subject, comprising administering to the subject 2-chloro-N-[(1S)-1-(5-methyl-1,2,4-oxadiazol-3-yl)ethyl]-4-[7-(quinolin-6-ylmethyl)imidazo[1,2-b][1,2,4]triazin-2-yl]benzamide, or a pharmaceutically acceptable salt thereof, such that the cancer is treated.

In another embodiment, provided herein is a method of treating cancer in a subject comprising administering to the subject N-methyl-5-[7-(quinolin-6-ylmethyl)imidazo[1,2-b][1,2,4]triazin-2-yl]pyridine-2-carboxamide, or a pharmaceutically acceptable salt thereof, such that the cancer is treated.

In another embodiment, provided herein is a method of treating cancer in a subject in need thereof, comprising administering to the subject N,2-dimethyl-4-[7-(quinolin-6-ylmethyl)imidazo[1,2-b][1,2,4]triazin-2-yl]benzamide, or a pharmaceutically acceptable salt thereof, such that the cancer is treated.

Thus, in one embodiment, provided herein is a method of inhibiting tumor growth in a subject in need thereof, comprising administering to the subject 2-fluoro-N-[(2R)-2-hydroxypropyl]-4-[7-(quinolin-6-ylmethyl)imidazo[1,2-b][1,2,4]triazin-2-yl]benzamide, or a pharmaceutically acceptable salt thereof.

In another embodiment, provided herein is a method of inhibiting tumor growth in a subject in need thereof, comprising administering to the subject 2-chloro-N-methyl-4-(7-(quinolin-6-ylmethyl)imidazo[1,2-b][1,2,4]triazin-2-yl)benzamide, or a pharmaceutically acceptable salt thereof.

In another embodiment, provided herein is a method of inhibiting tumor growth in a subject in need thereof, comprising administering to the subject 2-chloro-N-[(1S)-1-(5-methyl-1,2,4-oxadiazol-3-yl)ethyl]-4-[7-(quinolin-6-ylmethyl)imidazo[1,2-b][1,2,4]triazin-2-yl]benzamide, or a pharmaceutically acceptable salt thereof.

In another embodiment, provided herein is a method of inhibiting tumor growth in a subject in need thereof, comprising administering to the subject N-methyl-5-[7-(quinolin-6-ylmethyl)imidazo[1,2-b][1,2,4]triazin-2-yl]pyridine-2-carboxamide, or a pharmaceutically acceptable salt thereof, such that the cancer is treated.

In another embodiment, provided herein is a method of inhibiting tumor growth in a subject in need thereof, comprising administering to the subject N,2-dimethyl-4-[7-(quinolin-6-ylmethyl)imidazo[1,2-b][1,2,4]triazin-2-yl]benzamide, or a pharmaceutically acceptable salt thereof.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vive system. For example, "contacting" a compound of the invention with a protein kinase includes the administration of a compound of the present invention to an individual or patient, such as a human, as well as, for example, introducing a compound of the invention into a sample containing a cellular or purified preparation of the protein kinase.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following: (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

The term "treated," "treating" or "treatment" includes the diminishment or alleviation of at least one symptom associated with the activity of c-Met kinase, the HGF/c-Met kinase signaling pathway, and/or the proliferative activity of a cell. The term "treated," "treating" or "treatment" as used in reference to a disease or condition shall mean to intervene in such disease or condition so as to prevent or slow the development of, prevent or slow the progression of, halt the progression of, or eliminate the disease or condition.

The term "use" includes any one or more of the following embodiments of the invention, respectively: the use in the treatment of a disorder; the use for the manufacture of pharmaceutical compositions for use in the treatment of a disorder, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise. In particular, diseases to be treated and are thus preferred for use of a compound of the present invention are selected from diseases associated with the activity of c-Met kinase, the HGF/c-Met kinase signaling pathway, and/or the proliferative activity of a cell, and cancer.

Combination Therapy

One or more additional pharmaceutical agents or treatment methods such as, for example, chemotherapeutics, anti-cancer agents, cytotoxic agents, or anti-cancer therapies (e.g., radiation, hormone, etc.), can be used in combination with the compounds and salts of the present invention for treatment of the diseases, disorders or conditions described herein. The agents or therapies can be administered together with the compounds or salts of the invention (e.g., combined into a single dosage form), or the agents or therapies can be administered simultaneously or sequentially by separate routes of administration.

Suitable anti-cancer agents include kinase inhibiting agents including trastuzumab (Herceptin), imatinib (Gleevec), gefitinib (Iressa), erlotinib hydrochloride (Tarceva), cetuximab (Erbitux), bevacizumab (Avastin), sorafenib (Nexavar), sunitinib (Sutent), and RTK inhibitors described in, for example, WO 2005/004808, WO 2005/004607, WO 2005/005378, WO 2004/076412, WO 2005/121125, WO 2005/039586, WO 2005/028475, WO 2005/040345, WO 2005/039586, WO 2003/097641, WO 2003/087026, WO 2005/040154, WO 2005/030140, WO 2006/014325, WO 2005/070891, WO 2005/073224, WO 2005/113494, and US Pat. App. Pub. Nos. 2005/0085473, 2006/0046991, and 2005/0075340.

Suitable chemotherapeutic or other anti-cancer agents further include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Suitable chemotherapeutic or other anti-cancer agents further include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol™), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-β, etc.). Further antibody therapeutics include antibodies to tyrosine kinases and/or their ligands such as anti-HGF antibodies and/or anti-c-Met antibodies. The term "antibody" is meant to include whole antibodies (e.g., monoclonal, polyclonal, chimeric, humanized, human, etc.) as well as antigen-binding fragments thereof.

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Other anti-cancer agents include anti-cancer vaccines such as dendritic cells, synthetic peptides, DNA vaccines and recombinant viruses.

Methods for the safe and effective administration of most of the above agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds or salts of the invention can be administered in the form of pharmaceutical compositions corresponding to a combination of a compound of the invention (or salt thereof) and a pharmaceutically acceptable carrier. These compositions can be prepared in a manner well known in the pharmaceutical arts, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer, intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 500 mg, more usually about 10 to about 100 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as anti-viral agents, vaccines, antibodies, immune enhancers, immune suppressants, anti-inflammatory agents and the like.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results. The compounds of the Examples were found to be inhibitors of c-Met according to one or more of the assays provided herein.

EXAMPLES

Experimental procedures for compounds of the invention are provided below. Generally, the product was purified on a preparative scale by high performance liquid chromatography (HPLC) or flash chromatography (silica gel) as indicated in the Examples. Typical preparative reverse-phase high performance liquid chromatography (RP-HPLC) column conditions were as follows:

pH=2 purifications: Waters Sunfire™ $C_{18}$ 5 Tm, 19×100 mm column, eluting with mobile phase A: 0.1% TFA (trifluoroacetic acid) in water and mobile phase B: 0.1% TFA in acetonitrile; the flow rate is 30 ml/m; the separating gradient is optimized for each compound using the Compound Specific Method Optimization protocol as described in the literature ["Preparative LCMS Purification: Improved Compound Specific Method Optimization", K. Blom, B. Glass, R. Sparks, A. Combs, *J. Comb. Chem.*, 6, 874-883 (2004)].

pH=10 purifications: Waters XBridge $C_{18}$ 5 Tm, 19×100 mm column, eluting with mobile phase A: 0.15% $NH_4OH$ in water and mobile phase B: 0.15% $NH_4OH$ in acetonitrile; the flow rate was 30 ml/m; the separating gradient is optimized for each compound using the Compound Specific Method Optimization protocol as described in the literature ["Preparative LCMS Purification: Improved Compound Specific Method Optimization", K. Blom, B. Glass, R. Sparks, A. Combs, *J. Comb. Chem.*, 6, 874-883 (2004)].

The separated isomers were typically subjected to analytical liquid chromatography mass spectrometry (LCMS) for purity under the following conditions: Instrument; Agilent 1100 series, LC/MSD, Column: Waters Sunfire™ $C_{18}$ 5 Tm, 2.1×5.0 mm, Buffers: mobile phase A: 0.025% TFA in water and mobile phase B: 0.025% TFA in acetonitrile; gradient 2% to 80% of B in 3 min with flow rate 1.5 mL/min.

Example 1

2-Fluoro-N-[(2R)-2-hydroxypropyl]-4-[7-(quinolin-6-ylmethyl)imidazo[1,2-b][1,2,4]triazin-2-yl]benzamide

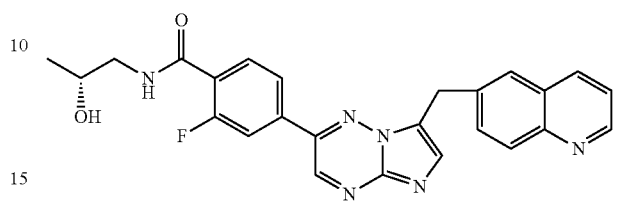

Step 1:
4-Bromo-3-fluoro-N-methoxy-N-methylbenzamide

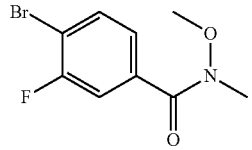

Oxalyl chloride (38.1 mL, 450 mmol) was slowly added to a mixture of 4-bromo-3-fluorobenzoic acid (49.3 g, 225 mmol) (Alfa Aesar, Cat.#B25475) in dichloromethane (300 mL). Subsequently, N,N-dimethylformamide (1.0 mL) was added and the reaction mixture was stirred at ambient temperature for 2 h. The reaction mixture was concentrated under reduced pressure and co-evaporated with toluene 3 times. The residue was then dissolved in dichloromethane (100 mL). The solution was added drop-wise to a mixture of N,O-dimethylhydroxylamine hydrochloride (30.7 g, 315 mmol) and potassium carbonate (120 g, 900 mmol) in dichloromethane (300 mL) and water (300 mL). The reaction mixture was stirred at ambient temperature for 2 hours. The organic layer was separated. The aqueous layer was extracted with dichloromethane (2×50 mL). The combined organic extracts were washed with brine, dried over magnesium sulfate, filtered and concentrated under reduced pressure to give the product. (58.5 g) LCMS (M+H)$^+$: m/z=261.9/263.9.

Step 2: 1-(4-Bromo-3-fluorophenyl)ethanone

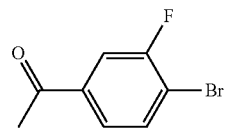

To a solution of 4-bromo-3-fluoro-N-methoxy-N-methylbenzamide (Step 1, 58.5 g, 223 mmol) in tetrahydrofuran (500 mL) was added 3M of methylmagnesium chloride in THF (125 mL, 380 mmol) at 0° C. The reaction mixture was stirred for 1 hour at 0° C., and was quenched with cold aqueous ammonium chloride solution (150 mL). The organic layer was separated and concentrated under reduced pressure. The residue was re-dissolved in ethyl acetate (100 mL). The aqueous layer was diluted with water (100 mL) and was extracted with ethyl acetate (3×50 mL). The organic extracts were combined, washed with brine, and dried over magnesium sulfate. Filtration and concentration under reduced pressure gave the product (48.4 g) which was used in the next reaction step without further purification.

Step 3: (4-Bromo-3-fluorophenyl)(oxo)acetaldehyde and 1-(4-bromo-3-fluorophenyl)-2,2-dihydroxyethanone

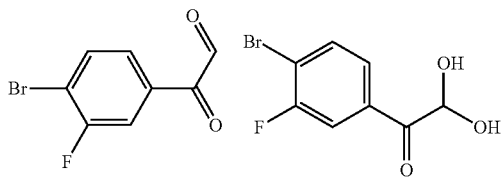

To a solution of 1-(4-bromo-3-fluorophenyl)ethanone (Step 2, 9.0 g, 41 mmol) in dimethyl sulfoxide (40 mL) was added slowly a 48% aqueous solution of hydrogen bromide. (14 mL) The reaction mixture was stirred at 60° C. overnight and then cooled to ambient temperature, and poured into ice water. The precipitate was filtered and washed with water and the solid was dried under vacuum overnight to obtain 8.1 g of desired product. The aqueous layer was extracted with ethyl acetate 3 times. The combined extracts were washed with water, brine, dried, filtered, and concentrated to give an additional 2.2 g of the desired product (10.3 g total).

Step 4: 1-(4-Bromo-3-fluorophenyl)-2,2-diethoxyethanone

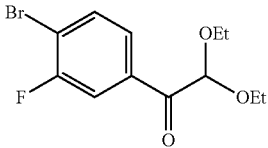 [SMILES: CCOC(OCC)C(=O)c1ccc(Br)c(F)c1]

To a mixture of 1-(4-bromo-3-fluorophenyl)-2,2-dihydroxyethanone and 4-bromo-3-fluorophenyl)(oxo)acetaldehyde (crude product from Step 3, 7.0 g, 28 mmol) in toluene (50 mL) was added ethyl orthoformate (12 mL, 70 mmol) and p-toluenesulfonic acid (200 mg, 1 mmol). The reaction mixture was refluxed for 4 h. The reaction mixture was cooled to RT, diluted with ethyl acetate, washed with aqueous sodium bicarbonate, water, brine, and dried over magnesium sulfate. Concentration under reduced pressure gave the desired product which was used in the next step without further purification.

Step 5: 6-(4-Bromo-3-fluorophenyl)-1,2,4-triazin-3-amine

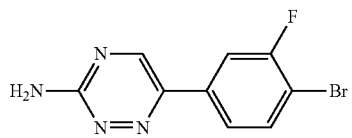 [SMILES: Nc1ncc(-c2ccc(Br)c(F)c2)nn1]

A mixture of 1-(4-bromo-3-fluorophenyl)-2,2-diethoxyethanone (Step 4, 15.2 g, 50 mmol), aminoguanidine bicarbonate (10.2 g, 75 mmol) and potassium hydroxide (6.6 g, 100 mmol) in ethanol (200 mL) and water (4 mL) was refluxed overnight. The solvent was evaporated under reduced pressure and the residue was washed with acetonitrile and filtered. The filtrate was concentrated under reduced pressure. The residue was dissolved in dichloromethane (100 mL), washed with water, brine, and concentrated under reduced pressure. The residue was dissolved in ethanol (50 mL). To the solution was added 0.2N hydrochloric acid (50 mL). The resultant mixture was heated to 110° C. for 8 h, and cooled with an ice-water bath. The precipitate that formed was collected by filtration and washed with isopropanol to give the desired product. (5.5 g, 41%) LCMS: (M+H) 286.8/288.8. $^1$H-NMR (400 MHz, CDCl$_3$): 8.60 (s, 1H), 7.79 (dd, J=8.6, 2.0 Hz, 1H), 7.68 (dd, J=8.3, 7.0 Hz, 1H), 7.61 (dd, J=8.3, 2.0 Hz, 1H), 5.43 (s, 2H).

Step 6: 3-Quinolin-6-ylpropnal

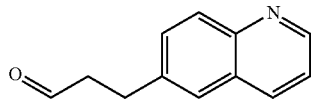 [SMILES: O=CCCc1ccc2ncccc2c1]

Tris(dibenzylideneacetone)dipalladium (480 mg, 0.52 mmol) (Aldrich, Cat. #328774) and tri-tert-butyl-phosphonium tetrafluoroborate (300 mg, 1.0 mmol) in a flask was evacuated and refilled with nitrogen (2 times). 1,4-Dioxane (31 mL) was added followed by consecutive addition of 6-bromoquinoline (7.2 g, 35 mmol) (TCI, Cat. #B2015), 2-propen-1-ol (4.7 mL, 69 mmol) and N-cyclohexyl-N-methyl-cyclohexanamine (8.9 mL, 42 mmol). The reaction vessel was evacuated and refilled with nitrogen (2 times). The reaction mixture was stirred at 30° C. for 24 h. Diethyl ether (30 mL) was added to the reaction mixture and then filtered and washed with diethyl ether. The organic extract was concentrated under reduced pressure. The residue was purified by flash chromatography eluting with ethyl acetate in hexanes (0-50%) to afford the desired product. (~55%) LCMS (M+H)$^+$: m/z=186.0; (M+H$_2$O+H)$^+$: m/z=204.0.

Step 7: 1-(2-Chloro-1-hydroxy-3-quinolin-6-ylpropyl)pyrrolidine-2,5-dione

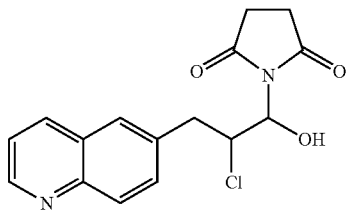 [SMILES: O=C1CCC(=O)N1C(O)C(Cl)Cc1ccc2ncccc2c1]

To a solution of 3-quinolin-6-ylpropanal (Step 6, 2.3 g, 0.012 mol) in chloroform (5 mL) cooled at 0° C. was added L-proline (0.4 g, 0.004 mol). To the mixture was then added N-chlorosuccinimide (1.74 g, 0.0130 mol) at 0° C. The reaction was warmed to r.t. and stirred overnight. The reaction was thick slurry. Solid was filtered and was washed with chloroform to give the pure product (2 g, 50.5%).

¹H-NMR (300 MHz, CDCl₃): 8.90 (dd, J=4.0, 2.0 Hz, 1H), 8.13 (d, J=8.0 Hz, 1H), 8.05 (d, J=8.4 Hz, 1H), 7.73 (s, 1H), 7.65 (dd, J=8.0, 2.0 Hz, 1H), 7.40 (dd, J=8.4, 4.0 Hz, 1H), 5.46 (d, J=9.4 Hz, 1H), 4.95 (ddd, J=9.4, 8.0, 3.1 Hz, 1H), 3.73 (dd, J=14.3, 3.1 Hz, 1H), 3.19 (dd, J=14.3, 8.0 Hz, 1H), 2.75 (s, 4H).

Step 8: 6-[2-(4-Bromo-3-fluorophenyl)imidazo[1,2-b][1,2,4]triazin-7-yl]methylquinoline

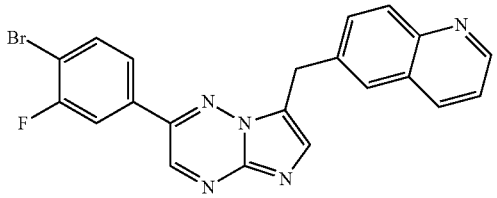 [SMILES: Fc1cc(-c2cnc3ncc(Cc4ccc5ncccc5c4)n3n2)ccc1Br]

A mixture of 6-(4-bromo-3-fluorophenyl)-1,2,4-triazin-3-amine (Step 5, 200 mg, 0.743 mmol) and 1-(2-chloro-1-hydroxy-3-quinolin-6-ylpropyl)pyrrolidine-2,5-dione (Step 7, 284 mg, 0.892 mmol) in isopropyl alcohol (7.4 mL) and water (0.11 mL) in a sealed tube was heated at 105° C. for 5 d. After the reaction mixture was cooled to ambient temperature, the precipitate was collected by filtration, washed with isopropanyl alcohol, and dried in vacuum to give the desired product (180 mg, 55%) LCMS (M+H)⁺: m/z=433.9/436.0.

Step 9: 2-Fluoro-4-[7-(quinolin-6-ylmethyl)imidazo[1,2-b][1,2,4]triazin-2-yl]benzonitrile

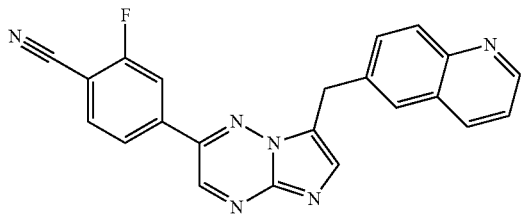 [SMILES: N#Cc1ccc(-c2cnc3ncc(Cc4ccc5ncccc5c4)n3n2)cc1F]

Zinc cyanide (131 mg, 1.11 mmol), tris(dibenzylideneacetone)dipalladium(0) (35 mg, 0.038 mmol) (Aldrich, Cat. #328774), (9,9-dimethyl-9H-xanthene-4,5-diyl)bis(diphenylphosphine) (78.5 mg, 0.136 mmol) (Aldrich, Cat. #526460), and N,N,N',N'-tetramethylethylenediamine (0.22 mL, 1.4 mmol) were added successively to a mixture of 6-[2-(4-bromo-3-fluorophenyl)imidazo[1,2-b][1,2,4]-triazin-7-yl]methylquinoline (Step 8, 480 mg, 1.10 mmol) in N,N-dimethylformamide (8.7 mL) in a microwave tube. The tube was sealed and degassed three times and heated to 160° C. under microwave irradiation for 500 s. Most of the solvent was removed under reduced pressure and the residue was dissolved in ethyl acetate, washed with aqueous sodium bicarbonate, water and brine, and dried over magnesium sulfate. Filtration and concentration afforded a residue which was purified on a silica gel column with methanol in dichloromethane (0-6%) to give the desired product. (90%) LCMS (M+H)⁺: m/z=381.0.

Step 10: 2-Fluoro-4-[7-(quinolin-6-ylmethyl)imidazo[1,2-b][1,2,4]triazin-2-yl]benzoic acid

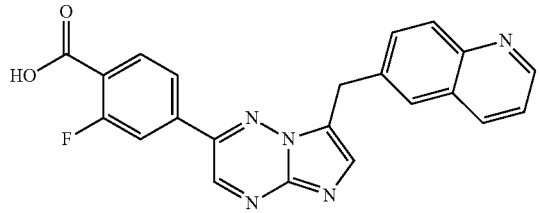 [SMILES: O=C(O)c1ccc(-c2cnc3ncc(Cc4ccc5ncccc5c4)n3n2)cc1F]

2-Fluoro-4-[7-(quinolin-6-ylmethyl)imidazo[1,2-b][1,2,4]triazin-2-yl]benzonitrile (Step, 9, 750 mg, 2 mmol) in a concentrated solution of hydrochloric acid (5.0 mL, 53 mmol) and water (1.0 mL) was stirred at 105° C. overnight. The solvent was removed under reduced pressure and the resultant residue was washed with water and filtered to provide the crude product as the HCl salt which was directly used in next reaction step without further purification. LCMS (M+H)⁺: m/z=400.0.

Step 11: 2-Fluoro-N-[(2R)-2-hydroxypropyl]-4-[7-(quinolin-6-ylmethyl)imidazo[1,2-b][1,2,4]triazin-2-yl]benzamide

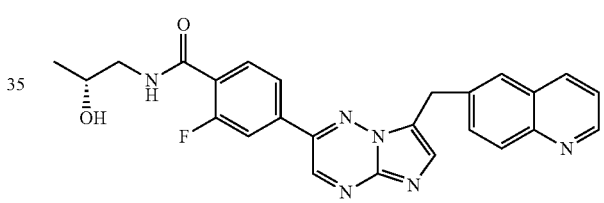

A mixture of 2-fluoro-4-[7-(quinolin-6-ylmethyl)imidazo[1,2-b][1,2,4]triazin-2-yl]benzoic acid HCl salt (180.0 mg, 0.381 mmol, Step 10) and benzotriazol-1-yloxytris(dimethylamino)phosphonium hexafluorophosphate (220 mg, 0.50 mmol) (Aldrich, Cat. #226084) in N,N-dimethylformamide (9.0 mL) was stirred at r.t. for 3 min. (2R)-1-Aminopropan-2-ol (57 mg, 0.76 mmol) was then slowly added followed by triethylamine (318.7 µL, 2.287 mmol). The mixture was stirred at r.t. for 3 h., and then water was added. The precipitate was collected by filtration and washed with aqueous acetonitrile. The precipitate was dissolved in 1 N HCl aqueous solution, and then dried by lyophilization to give the desired product as the HCl salt. LCMS (M+H)⁺: m/z=457.3. ¹H-NMR (500 MHz, DMSO-d₆): 9.30 (s, 1H), 9.20 (dd, J=5.0, 1.5 Hz, 1H), 9.02 (d, J=8.0 Hz, 1H), 8.37 (s, 1H), 8.35 (d, J=8.0 Hz, 1H), 8.28 (s, 1H), 8.16 (dd, J=8.5, 1.5 Hz, 1H), 8.08 (s, 1H), 8.04 (s, 1H), 8.02 (s, 1H), 8.00 (dd, J=8.5, 5.0, Hz, 1H), 7.80 (t, J=8.0 Hz, 1H), 4.75 (s, 2H), 3.79 (m, 1H), 3.21 (m, 2H), 1.09 (d, J=7.0 Hz, 3H).

The S enantiomer can be made according to the above procedure using (2S)-1-aminopropan-2-ol or by racemizing the product and separating enantiomers using standard chiral separation techniques (e.g., a chiral column).

Example 2

2-Chloro-N-methyl-4-(7-(quinolin-6-ylmethyl)imidazo[1,2-b][1,2,4]triazin-2-yl)benzamide

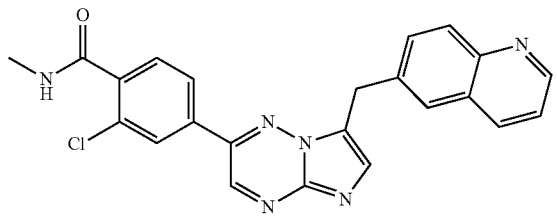 [SMILES: CNC(=O)c1ccc(-c2cnc3ncc(Cc4ccc5ncccc5c4)n3n2)cc1Cl]

Step 1: 6-Bromo-1,2,4-triazin-3-amine

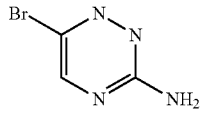

To a suspension of 1,2,4-triazin-3-amine (3.84 g, 40.0 mmol) (Aldrich, Cat. #100625) in acetonitrile (40 mL) was added water (60 mL) and stirred until a clear solution was formed. To this solution was added N-bromosuccinimide (7.48 g, 42.0 mmol) at 0° C. and the resulting mixture was stirred for 10 min. The cooling bath was removed, and the mixture was allowed to warm to room temperature. The mixture was then diluted with ethyl acetate (150 mL) and cooled to 0° C. (ice-water bath). Na$_2$CO$_3$ (3.0 g) was added and stirred for 10 min. The two layers were separated and the aqueous phase was extracted with ethyl acetate (150 mL). The combined organic layers were washed with sat'd NaHCO$_3$, brine, dried over MgSO$_4$, and filtered. The filtrate was concentrated under reduced pressure to afford the desired product (4 g, 57.15%). LCMS (M+H)$^+$: m/z=175.2/177.2.

Step 2: Methyl 4-(3-amino-1,2,4-triazin-6-yl)-2-chlorobenzoate

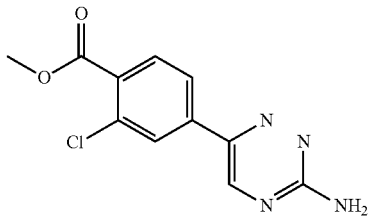 [SMILES: COC(=O)c1ccc(/C(N)=C/N=C(N)N)cc1Cl]

To a mixture of 6-bromo-1,2,4-triazin-3-amine (Step 1, 1.0 g, 5.7 mmol) and [3-chloro-4-(methoxycarbonyl)phenyl]boronic acid (1.5 g, 6.8 mmol) (VMR, Cat. #100013-404) in 1,4-dioxane (22 mL) was added a solution of potassium phosphate (2.4 g, 11 mmol) in water (5.1 mL). The mixture was degassed by purging nitrogen for 10 min. To the mixture was added tetrakis(triphenylphosphine)palladium(0) (0.20 g, 0.17 mmol) and again was degassed with nitrogen. The mixture was stirred and heated at 82° C. (an oil bath) for 1 h. The mixture was cooled to r.t., diluted with water, stirred for 30 min, and a grey solid formed. The solid was isolated by filtration, rinsed several times with water, and dried in air. The solid was then triturated sequentially with hexanes, dichloromethane-hexanes (1:1), and hexanes to afford the desired product (840 mg, 55.54%). LCMS (M+H)$^+$: m/z=264.9/267.0.

Step 3: Methyl 2-chloro-4-[7-(quinolin-6-ylmethyl)imidazo[1,2-b][1,2,4]triazin-2-yl]benzoate

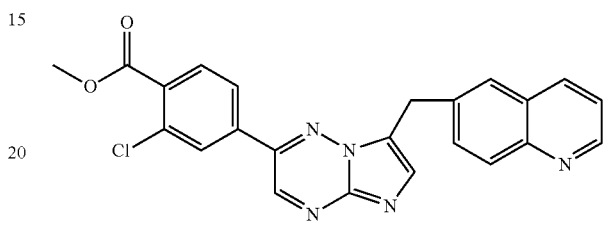

The mixture of methyl 4-(3-amino-1,2,4-triazin-6-yl)-2-chlorobenzoate (Step 2, 0.840 g, 3.17 mmol) and 1-(2-chloro-1-hydroxy-3-quinolin-6-ylpropyl)pyrrolidine-2,5-dione (1.11 g, 3.49 mmol, Example 1, Step 7) in 1-butanol (11.6 mL) was stirred at 110° C. for 22 h. The solvent was removed under reduced pressure. The residue was triturated with ethyl acetate. The precipitate was collected by filtration and washed with ethyl acetate and hexane to yield the desired product (0.908 g). The mother liquor was concentrated to half volume. The precipitate was collected by filtration and washed with ethyl acetate and hexane to afford additional desired product (0.342 g). The total product obtained was 1.10 g (80.6%). LCMS (M+H)$^+$: m/z=430.0/431.9.

Step 4: 2-Chloro-4-[7-(quinolin-6-ylmethyl)imidazo[1,2-b][1,2,4]triazin-2-yl]benzoic acid

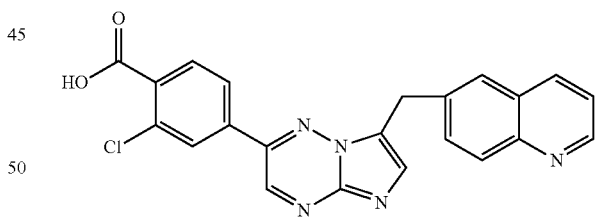

To a solution of methyl 2-chloro-4-[7-(quinolin-6-ylmethyl)imidazo[1,2-b][1,2,4]triazin-2-yl]benzoate (Step 3, 1.10 g, 2.56 mmol) in tetrahydrofuran (7.0 mL) and methanol (5.0 mL) was added a solution of lithium hydroxide (0.245 g, 10.2 mmol) in water (3.0 mL). The mixture was stirred at room temperature for 2 h. and concentrated under reduced pressure to a volume of about 3 mL. The residue was diluted with water (3 mL), and adjusted with 1N HCl to pH of about 4-5. The precipitate was filtered out, washed several times with water and dried in air overnight. The precipitate was then triturated sequentially with ether and dichloromethane (DCM)-Hexane (1:1). The desired product (638 mg, 60%) was obtained. LCMS (M+H)$^+$: m/z=415.9/417.9.

Step 5: 2-Chloro-N-methyl-4-(7-(quinolin-6-ylmethyl)imidazo[1,2-b][1,2,4]triazin-2-yl)benzamide

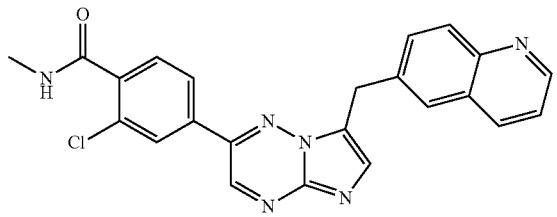 [SMILES: CNC(=O)c1ccc(-c2cnc3ncc(Cc4ccc5ncccc5c4)n3n2)cc1Cl]

2-Chloro-4-[7-(quinolin-6-ylmethyl)imidazo[1,2-b][1,2,4]triazin-2-yl]benzoic acid (Step 4, 5.0 mg, 0.012 mmol) and (benzotriazol-1-yloxy)tripyrrolidinophosphonium hexafluorophosphate (10.0 mg, 0.020 mmol) (Aldrich, Cat. #226084) in N,N-dimethylformamide (0.5 mL) was stirred at r.t. for 3 min. 2.0 M of Methylamine in tetrahydrofuran (0.012 mL, 0.023 mmol) was then slowly added at 0° C. followed by triethylamine (6.4 µL, 0.046 mmol). The mixture was stirred at r.t. for 2 h., and purified by RP-HPLC (pH=2) to afford the desired product as the trifluoroacetate (TFA) salt. LCMS (M+H)$^+$: m/z=429.3.

Example 3

2-Chloro-N-[(1S)-1-(5-methyl-1,2,4-oxadiazol-3-yl)ethyl]-4-[7-(quinolin-6-ylmethyl)imidazo[1,2-b][1,2,4]triazin-2-yl]benzamide

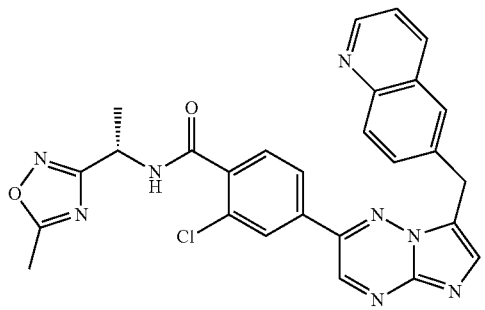 [SMILES: Cc1nc([C@H](C)NC(=O)c2ccc(-c3cnc4ncc(Cc5ccc6ncccc6c5)n4n3)cc2Cl)no1]

Step 1: tert-Butyl [(1S)-2-amino-1-methyl-2-oxoethyl]carbamate

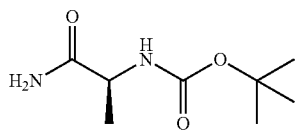

To a stirred solution of (2S)-2-[(tert-butoxycarbonyl)amino]propanoic acid (1 g, 0.005 mol) in THF at 0° C. was added 4-methylmorpholine (0.588 g, 0.00581 mol) followed by dropwise addition of isobutyl chloroformate (0.794 g, 0.00581 mol) over 2 min. The reaction was stirred at 0° C. for 30 min. after which a solution of 30 wt. % ammonium hydroxide (12.0 mL, 0.0925 mol) was quickly poured into the reaction. The reaction was warmed to room temperature and stirred for 5 h. The reaction mixture was concentrated. Water was added and the mixture extracted with ethyl acetate. The combined organic layers were washed with brine, dried over MgSO$_4$, filtered and concentrated to afford the crude product which was directly used in the next step reaction without further purification (800 mg, 80%). $^1$H-NMR (300 MHz, DMSO-d$_6$): 12.40 (s, 1H), 7.10 (d, J=7.0 Hz, 1H), 3.88 (m, 1H), 1.35 (s, 9H), 1.20 (d, J=7.3 Hz, 3H).

Step 2: tert-Butyl [(1S)-1-cyanoethyl]carbamate

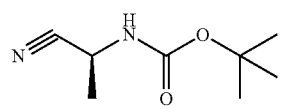

To a stirred solution of tert-butyl [(1S)-2-amino-1-methyl-2-oxoethyl]carbamate (Step 1, 0.7 g, 0.004 mol) in N,N-dimethylformamide (5 mL) was added 343 mg of cyanuric chloride (0.00186 mol) at once. The reaction mixture was stirred for 4 h. Water was added and the mixture was extracted with ethyl acetate. The combined organic layers were washed with brine, dried over MgSO$_4$, filtered, and concentrated under reduced pressure. The residue was purified by flash chromatography on a silica gel column with EtOAc in hexane (30-50%) to yield the desired product (400 mg, 63%). $^1$H-NMR (300 MHz, DMSO-d$_6$): 7.74 (d, J=7.0 Hz, 1H), 4.48 (m, 1H), 1.40 (s, 9H), 1.35 (d, J=7.0 Hz, 3H).

Step 3: tert-Butyl [(1S,2Z)-2-amino-2-(hydroximino)-1-methylethyl]carbamate

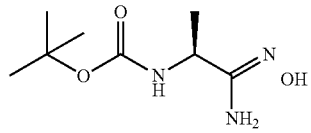

To a mixture of tert-butyl [(1S)-1-cyanoethyl]carbamate (Step 2, 250 mg, 1.5 mmol) in ethanol (3 mL) were added triethylamine (0.41 mL, 2.9 mmol) and hydroxylamine (58 mg, 1.8 mmol). The mixture was stirred at 50° C. overnight. The reaction mixture was concentrated to afford the desired crude product (300 mg) which was directly used in the next step reaction without further purification. $^1$H-NMR (300 MHz, DMSO-d$_6$): 8.94 (s, 1H), 6.80 (d, J=8.5 Hz, 1H), 5.24 (s, 2H), 4.01 (m, 1H), 1.36 (s, 9H), 1.15 (d, J=7.0 Hz, 3H).

Step 4: tert-Butyl {(1S,2Z)-2-[(acetyloxy)imino]-2-amino-1-methylethyl}carbamate

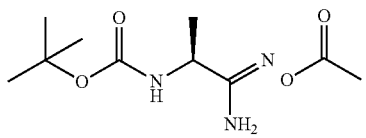

To a mixture of tert-butyl [(1S,2Z)-2-amino-2-(hydroxyimino)-1-methylethyl]carbamate (Step 3, 100 mg, 0.5 mmol) in methylene chloride (2 mL) cooled at 0° C. was added triethylamine (0.10 mL, 0.74 mmol). To the mixture was then added acetyl chloride (42 mg, 0.54 mmol) dropwise and the reaction was warmed to room temperature. After stirring at room temperature for 1 h, the reaction was concentrated. The residue was dissolved in dichloromethane (DCM), washed with water and brine, dried over MgSO$_4$, filtered and concentrated to afford the desired crude product (100 mg, 82.8%) which was directly used in the next step reaction without further purification. $^1$H-NMR (300 MHz, DMSO-d$_6$): 6.90 (d, J=9.0 Hz, 1H), 6.22 (s, 2H), 4.05 (m, 1H), 2.01 (s, 3H), 1.36 (s, 9H), 1.20 (d, J=7.0 Hz, 3H).

Step 5: (1S)-1-(5-Methyl-1,2,4-oxadiazol-3-yl)ethanamine

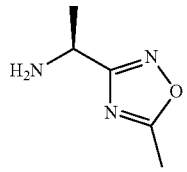

To a solution of tert-butyl {(1 S,2Z)-2-[(acetyloxy)imino]-2-amino-1-methylethyl}carbamate (Step 4, 80 mg, 0.3 mmol) in ethanol (3 mL) was added a solution of sodium acetate trihydrate (49 mg, 0.36 mmol) in water (1 mL). The mixture was heated at 85° C. for 3 h. Ethanol was evaporated; water was added and extracted with EtOAc. The combined organic layers were washed with brine, dried over MgSO$_4$, filtered and concentrated. The residue was dissolved in methylene chloride (1 mL). To the solution was added trifluoroacetic acid (1 mL). After stirring 30 min., the reaction mixture was concentrated to afford the desired product as TFA salt which was directly used in the next step reaction without further purification Step 6: 2-Chloro-N-[(1S)-1-(5-methyl-1,2,4-oxadiazol-3-yl)ethyl]-4-[7-(quinolin-6-ylmethyl)imidazo[1,2-b][1,2,4]triazin-2-yl]benzamide

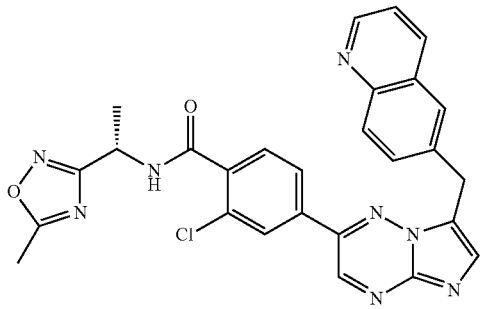 [SMILES: Cc1nc([C@H](C)NC(=O)c2ccc(-c3cnc4ncc(Cc5ccc6ncccc6c5)n4n3)cc2Cl)no1]

To a solution of 2-chloro-4-[7-(quinolin-6-ylmethyl)imidazo[1,2-b][1,2,4]triazin-2-yl]benzoic acid (50 mg, 0.1 mmol, Example 2, Step 4) in N,N-dimethylformamide (2 mL, 20 mmol) was added N,N,N',N'-tetramethyl-O-(7-azabenzotriazol-1-yl)uronium hexafluorophosphate (68 mg, 0.18 mmol) (Aldrich, Cat. #226084) and N,N-diisopropylethylamine (42 μL, 0.24 mmol). After stirring the solution for 15 min, (1S)-1-(5-methyl-1,2,4-oxadiazol-3-yl)ethanamine TFA salt (18 mg, 0.14 mmol, Step 5) was added and stirred overnight. The mixture was purified by RP-HPLC (pH=10) to give the desired product which was further purified by RP-HPLC (pH=2) to afford the desired pure product as the TFA salt. LCMS (M+H)$^+$: m/z=525.0/427.0. $^1$H-NMR (500 MHz, DMSO-d$_6$): 9.22 (s, 1H), 8.98 (dd, J=5.0, 1.5 Hz, 1H), 9.15 (d, J=8.0 Hz, 1H), 8.56 (d, J=8.5 Hz, 1H), 8.16 (d, J=2.0 Hz, 1H), 8.14 (dd, J=8.0, 1.5 Hz, 1H), 8.06 (s, 1H), 8.04 (d, J=9.0 Hz, 1H), 8.02 (s, 1H), 7.90 (dd, J=9.0, 2.0 Hz, 1H), 7.68 (dd, J=8.5, 5.0 Hz, 1H), 7.60 (d, J=8.0 Hz, 1H), 5.24 (m, 1H), 4.66 (s, 2H), 2.60 (s, 3H), 1.51 (d, J=7.0 Hz, 3H).

The R enantiomer can be made according to the above procedure using (1R)-1-(5-methyl-1,2,4-oxadiazol-3-yl)ethanamine or by racemizing the product and separating enantiomers using standard chiral separation techniques (e.g., a chiral column).

Example 4

N-Methyl-5-[7-(quinolin-6-ylmethyl)imidazo[1,2-b][1,2,4]triazin-2-yl]pyridine-2-carboxamide

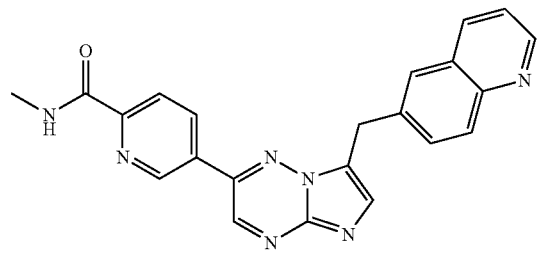 [SMILES: CNC(=O)c1ccc(-c2cnc3ncc(Cc4ccc5ncccc5c4)n3n2)cn1]

Step 1: 5-(3-Amino-1,2,4-triazin-6-yl)-N-methyl-pyridine-2-carboxamide

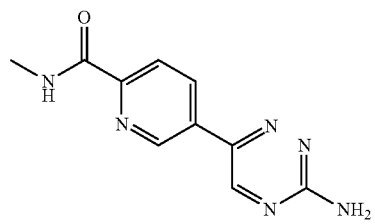 [SMILES: CNC(=O)c1ccc(C(=N)/C=N\C(=N)N)cn1]

A mixture of N-methyl-5-(4,4,5,5-tetramethyl-1,3,2-dioxaborolan-2-yl)pyridine-2-carboxamide (200 mg, 0.80 mmol) (VWR, Cat. #200068-640), 6-bromo-1,2,4-triazin-3-amine (130 mg, 0.76 mmol, Example 2, Step 1), tetrakis(triphenylphosphine)palladium(0) (40 mg, 0.04 mmol) and potassium carbonate (0.32 g, 2.3 mmol) in toluene (1.3 mL), ethanol (0.66 mL) and water (0.66 mL) was heated at 120° C. for 1.5 h. The mixture was filtered and washed with methanol. The filtrate was purified by RP-HPLC (pH=10) to afford the desired product (80 mg, 45.54%). LCMS (M+H)$^+$: m/z=231.4; LCMS (M+H+H$_2$O)$^+$: m/z=249.3.

Step 2: N-Methyl-5-[7-(quinolin-6-ylmethyl)imidazo[1,2-b][1,2,4]triazin-2-yl]pyridine-2-carboxamide

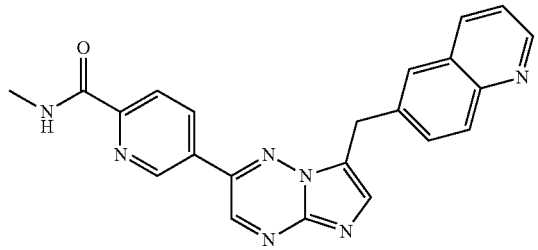 [SMILES: CNC(=O)c1ccc(-c2cnc3ncc(Cc4ccc5ncccc5c4)n3n2)cn1]

A mixture of 5-(3-amino-1,2,4-triazin-6-yl)-N-methylpyridine-2-carboxamide (Step 1, 6.5 g, 0.022 mol) and 1-(2-chloro-1-hydroxy-3-quinolin-6-ylpropyl)pyrrolidine-2,5-dione (8.71 g, 0.0273 mol, Example 1, Step 7) in 1,2-ethanediol (100 mL) was stirred at 120° C. overnight. The reaction mixture was concentrated. The mixture was neutralized to pH-10 with methylamine in THF solution (2.0M), and then purified by flash chromatography on a silica gel column with 5% MeOH in dichloromethane to afford the desired product which was contaminated with some starting material. The product was dissolved in 10% MeOH in dichloromethane, and concentrated to a volume of about 2 mL. The resulted solid was filtered, washed with MeOH (2 mL) to afford the pure product (4.50 g, 50%). The product was treated with 2N HCl (aqueous) and acetonitrile, and dried by lyophilization to give the desired product as the HCl salt. LCMS (M+H)$^+$: m/z=396.4. $^1$H-NMR (400 MHz, DMSO-$d_6$): 9.40 (s, 1H), 9.27 (s, 1H), 9.20 (d, J=5.5 Hz, 1H), 9.10 (d, J=8.0 Hz, 1H), 8.64 (d, J=8.0 Hz, 1H), 8.30 (s, 1H), 8.26 (d, J=8.0 Hz, 1H), 8.20 (d, J=8.0, Hz, 1H), 8.19 (s, 1H), 8.17 (d, J=8.0 Hz, 1H), 7.03 (dd, J=8.0, 5.5 Hz, 1H), 4.76 (s, 2H), 2.81 (s, 3H).

Example 5

N,2-Dimethyl-4-[7-(quinolin-6-ylmethyl)imidazo[1,2-b][1,2,4]triazin-2-yl]benzamide

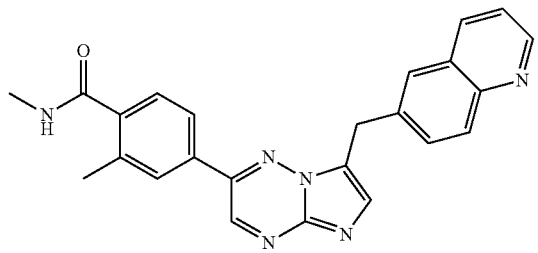 [SMILES: CNC(=O)c1ccc(-c2cnc3ncc(Cc4ccc5ncccc5c4)n3n2)cc1C]

Step 1: 4-Bromo-N,2-dimethylbenzamide

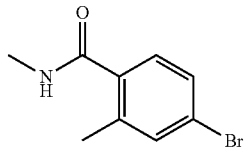

N,N-Dimethylformamide (10 μL) was added to a mixture of 4-bromo-2-methylbenzoic acid (1.0 g, 4.6 mmol) in oxalyl chloride (2.0 mL, 23 mmol). The mixture was stirred at room temperature overnight. The mixture was concentrated to afford a crude carbonyl chloride which was dissolved in methylene chloride (2 mL). The solution was added slowly to a mixture of methylamine in tetrahydrofuran (THF) (2.0 M, 0.465 mL, 9.3 mmol) and triethylamine (1.3 mL, 9.3 mmol) in DCM (10 ml). After 30 min, the reaction mixture was quenched with sat. sodium carbonate (10 mL) and extracted with DCM (3×20 mL). The combined organic layers were washed with brine, dried over Na$_2$SO$_4$, filtered, concentrated under reduced pressure to give a crude product (980 mg, 92%). LCMS (M+H)$^+$: m/z=228.1/230.2.

Step 2: N,2-Dimethyl-4-(4,4,5,5-tetramethyl-1,3,2-dioxaborolan-2-yl)benzamide

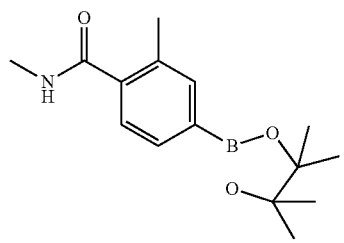

To a solution of 4-bromo-N,2-dimethylbenzamide (Step 1, 0.50 g, 2.2 mmol) and 4,4,5,5,4',4',5',5'-octamethyl-[2,2']bi[[1,3,2]dioxaborolanyl](0.67 g, 2.6 mmol) (Aldrich, Cat. #473294) in 1,4-dioxane (5.28 mL) was added [1,1'-bis(diphenylphosphino)-ferrocene]dichloropalladium(II) complex with dichloromethane (1:1) (0.09 g, 0.1 mmol) (Aldrich, Cat. #379670), potassium acetate (0.64 g, 0.0066 mol), and 1,1'-bis(diphenylphosphino)ferrocene (0.06 g, 0.1 mmol) (Aldrich, Cat. #177261) under an atmosphere of nitrogen. The reaction mixture was stirred at 80° C. overnight. After cooling to room temperature, the mixture was filtered, and concentrated under reduced pressure. The residue was purified by flash chromatography on a silica gel column with 10% methanol in dichloromethane to afford the desired product. LCMS (M+H)$^+$: m/z=276.4.

Step 3: 4-(3-Amino-1,2,4-triazin-6-yl)-N,2-dimethylbenzamide

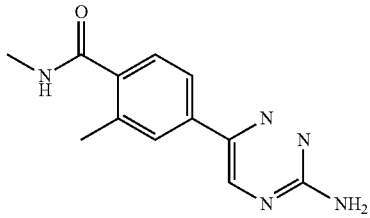 [SMILES: CNC(=O)c1ccc(/C(N)=C/N=C(N)N)cc1C]

A mixture of N,2-dimethyl-4-(4,4,5,5-tetramethyl-1,3,2-dioxaborolan-2-yl)benzamide (Step 2, 0.3 g, 0.001 mol), 6-bromo-1,2,4-triazin-3-amine (0.21 g, 1.2 mmol, Example 2, Step 1), tetrakis(triphenylphosphine)palladium(0) (0.06 g, 0.05 mmol) and potassium carbonate (0.45 g, 3.3 mmol) in toluene (1.9 mL), ethanol (0.94 mL) and water (0.94 mL). The resulting mixture was heated at 130° C. for 2.5 h. The mixture was diluted with MeOH, filtered, and washed with DCM/methanol (90%). The filtrate was concentrated. The residue was purified by flash chromatography on a silica gel column with 10% MeOH in DCM to afford the desired product (110 mg, 41%). LCMS (M+H)$^+$: m/z=244.3.

Step 4: 2-Chloro-3-quinolin-6-ylpropanal

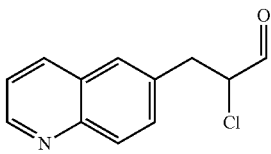 [SMILES: O=CC(Cl)Cc1ccc2ncccc2c1]

L-Proline (410 mg, 3.5 mmol) was added to a solution of 3-quinolin-6-ylpropanal (3.27 g, 17.6 mmol, Example 1, Step 6) in chloroform (39 mL) at 0° C. followed by addition of N-chlorosuccinimide (2.48 g, 18.5 mmol) and the reaction mixture was slowly warmed to ambient temperature and stirred for 1 h, monitoring by LCMS. The solvent was concentrated under reduced pressure and the residue was purified on a silica gel column with ethyl acetate in hexane (0-50%) to give the desired product. (95%) LCMS: (M+H+H$_2$O)=237.9/239.9.

Step 5: N,2-Dimethyl-4-[7-(quinolin-6-ylmethyl)imidazo[1,2-b][1,2,4]triazin-2-yl]benzamide

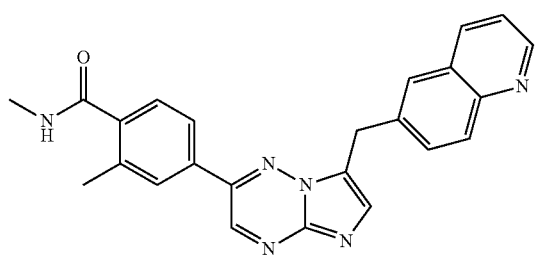 [SMILES: CNC(=O)c1ccc(-c2cnc3ncc(Cc4ccc5ncccc5c4)n3n2)cc1C]

A mixture of 4-(3-amino-1,2,4-triazin-6-yl)-N,2-dimethylbenzamide (Step 3, 0.30 g, 1.2 mmol) and 2-chloro-3-quinolin-6-ylpropanal (Step 4, 0.32 g, 1.5 mmol) in ethanol (2.5 mL) in a sealed tube was stirred at 120° C. overnight. After cooling, the reaction mixture was purified by RP-HPLC (pH=2) to afford the desired product (150 mg) as the TFA salt. LCMS (M+H)$^+$: m/z=409.3. $^1$H-NMR (400 MHz, CD$_3$OD): 9.64 (s, 1H), 9.21 (d, J=5.0, 1H), 9.18 (d, J=8.0 Hz, 1H), 8.44 (s, 1H), 8.39 (s, 1H), 8.32 (d, J=9.0 Hz, 1H), 8.27 (d, J=8.0 Hz, 1H), 8.12 (dd, J=9.0, 5.0, Hz, 1H), 8.05 (s, 1H), 8.03 (s, 1H), 7.57 (d, J=8.0 Hz, 1H), 4.86 (s, 2H), 2.92 (s, 3H), 2.48 (s, 3H).

Example A

In Vitro c-Met Kinase Enzyme Assays

The compounds of the invention were screened in vitro for their ability to inhibit c-Met kinase activity. The IC$_{50}$ values for the inhibition of c-Met kinase were determined as described in the literature with some modifications (Wang, X. et al, Mol. Cancer Ther. 2003, 2(11):1085-1092; Calic, M. et al., Croatica Chemical ACTA. 2005, 78(3):367-374). Briefly, histidine-tagged c-Met catalytic domain fusion protein (Invitrogen, #PV3143) was used for the assay. IC$_{50}$ measurements were based on the degree of phosphorylation of poly Glu-Tyr (Sigma-Aldrich, #P0275) that was coated (0.01 mg/per well) on 96-well microplates (R&D systems, #DY990). The reaction was carried out in a 50 μL solution containing 50 mM HEPES (pH 7.5), 10 mM MnCl$_2$, 10 mM MgCl$_2$, 0.5 mM DTT, 100 μM Na$_3$VO$_4$, 5 μM ATP (Cell Signaling Technology, #9804) and serial dilutions of the test compound. The reaction lasted for 25 minutes at 30° C. After the reaction was completed, the contents of the plates were discarded. Plates were then washed with TBS-T (250 μL/well, 5×) and then blocked with TBS-T containing 1% BSA for 2 hours. The contents of the plates was discarded, and 100 μL (per well) of peroxidase-labeled anti-phosphotyrosine antibody (Sigma, #A5964) diluted (1:60,000) in 1% BSA containing TBS-T were then added and incubated for 1 hour. Plates were washed with TBS-T (250 μL/well, 5×) and followed by the color reaction using 100 μL (1:1 mixture) of H$_2$O$_2$ and tetramethylbenzidine (R&D Systems, #DY999). The reaction was stopped in minutes with 100 μL of 2 N H$_2$SO$_4$. The optical density was measured immediately using a microplate reader at 450 nm with wavelength correction at 540 nm. IC$_{50}$ values were calculated with the GraphPad Prism software. The linear range (i.e., the time period over which the rate remained equivalent to the initial rate) was determined for the kinase and IC$_{50}$ determinations were performed within this range.

Wang, X., et al. Potent and selective inhibitors of the Met [hepatocyte growth factor/scatter factor (HGF/SF) receptor] tyrosine kinase block HGF/SF-induced tumor cell growth and invasion. Mol. Cancer Ther. 2003, 2(11):1085-1092.

Calic, M., et al. Flavonoids as inhibitors of Lck and Fyn kinases. Croatica Chemical ACTA. 2005, 78(3):367-374.

The IC$_{50}$ results for the compounds of the invention are shown below:

| Compound | IC$_{50}$ |
|---|---|
| Formula I | 0.1-1.0 nM |
| Formula II | 0.1-1.0 nM |
| Formula III | 0.1-1.0 nM |
| Formula IV | 0.1-1.0 nM |
| Formula V | 0.1-1.0 nM |

Example B

Cell Proliferation/Survival Assays

Cell lines representing various human cancers (SNU-1 and SUN-5 gastric, A549 and NCI-H441 lung, U-87 glioblastoma, HT-29 colon, 786-O kidney, PC-3 pancreatic) can be obtained from American Type Culture Collection and routinely maintained in culture media and conditions recommended by ATCC. Optimal cell density used in proliferation/survival assay can be predetermined for individual cell lines. Compounds are screened for their ability to inhibit cell proliferation/survival, and $IC_{50}$ values are determined. Below are the sample protocols for SNU-5 and SNU-1 cell proliferation/survival assays. SNU-5 and SNU-1 cells are seeded into 96 well cell culture plates at 4000 cells/well and 2000 cells/well respectively in appropriate media containing 2% FBS and supplemented with serial dilutions of individual compounds in a final volume of 100 µL/well. After 72 hour incubation, 24 µL of CellTiter 96@AQueous One Solution reagent (Promega, #G3381) are added to each well (final concentration=333 µg/mL), and the plates are incubated for 2 more hours in a 37° C. incubator. The optical density is measured in the linear range using a microplate reader at 490 nm with wavelength correction at 650 nm. $IC_{50}$ values are calculated with the GraphPad Prism software. For proliferation assays using A549, NCI-H441, U-87, HT-29, 786-0 and PC-3 cells, the cells are first starved for 48 hours in low serum condition (0.1-0.5% FBS in appropriate culture media), then treated with different concentrations of compounds for 2 hours. After the cells are treated with HGF (50 ng/mL) (R&D, #294-HGN) for 24 hours, CellTiter 96@ AQueous One Solution reagent is added and plates are incubated for 2 hours. The results are recorded with a plate reader.

Example C

Cell-Based c-Met Phosphorylation Assays

The inhibitory effect of compounds on c-Met phosphorylation in relevant cell lines (SNU-5 gastric, A549 and NCI-H441 lung, U-87 glioblastoma, HT-29 colon, 786-O kidney and PC-3 pancreatic cancer cell lines and HUVEC cell line) can be assessed using immunoblotting analysis and ELISA-based c-Met phosphorylation assays. Cells are grown in appropriate culture media and treated with various concentrations of individual compounds. For SNU-5, HT-29, 786-0 cells, cells are grown in appropriated media supplemented with 0.2% or 2% FBS and treated with compounds for 3-4 hours. Whole cell protein extracts are prepared using reagents and a protocol (#FNN0011) obtained from Biosource International with slight modifications. Briefly, protein extracts are made by incubation in lysis buffer with protease and phosphatase inhibitors [50 mM HEPES (pH 7.5), 100 mM NaCl, 1.5 mM $MgCl_2$, 10% Glycerol, 1% Triton X-100, 1 mM sodium orthovanadate, 1 mM sodium fluoride, aprotinin (2 µg/mL), leupeptin (2 µg/mL), pepstatin A (2 µg/mL), and phenylmethylsulfonyl fluoride (1 mM)] at 4° C. Protein extracts are cleared of cellular debris by centrifugation at 14,000×g for 20 minutes. For A549, H441, U-87 and PC-3 cells, cells are serum (0.2% FBS) starved for at least 24 hours, then pretreated with various concentrations of compounds for 1 hour. Whole cell extracts are prepared after the cells were treated with HGF (50 ng/mL) for 10 minutes.

Immunoblotting Analysis

Relevant antibodies are obtained from commercial sources: rabbit polyclonal antibodies included anti-human c-Met (Santa Cruz Biotechnology, #sc-161) and anti-phosphorylated-c-Met (Biosource International, pY1230/4/5 and pY1003). For immunoblotting, 10-20 µg of protein extracts from individual treatment conditions are resolved by electrophoresis on 10% SDS-PAGE gel, and electrotransferred to a nitrocellulose (or PVDF) membrane. The membrane is blocked in PBS containing 3% milk and 0.1% Tween-20 for 1 hour, and then incubated with primary anti-c-Met antibodies in blocking solution for 1 hour. After 3 washes, the membrane is incubated with appropriate horseradish-conjugated secondary antibodies for 1 hour. After final wash, the blot is incubated with chemiluminescence detection reagent for 5 minutes and exposed to X-ray film. The images are scanned, quantified and corrected with total c-Met, and $IC_{50}$ values are calculated. Compounds having an $IC_{50}$ of 10 µM or less are considered active.

ELISA

Cell protein extracts are analyzed using a human phospho-c-Met ELISA kit according to the manufacturer's instructions (R&D Systems, #DYC2480). Optimal amounts of protein extracts are predetermined for individual cell lines. Briefly, for the assay, appropriate amounts of protein extracts are captured with a capture anti-human c-Met antibody for 2 hours in a 96 well microplate. After washes, a detection antibody (HRP-conjugated anti-phospho-tyrosine antibody) is added and incubated for 2 hours. After additional washes, 100 µL of substrate solution (1:1 mixture of $H_2O_2$ and tetramethylbenzidine) are added into each well and the reaction is stopped with 2 N $H_2SO_4$ within an appropriate amount of time during color development. The optical density is measured in the linear range using a microplate reader at 450 nm with wavelength correction at 540 nm. $IC_{50}$ values are calculated with the GraphPad Prism software.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating gastric cancer, cancer of the kidney, liver cancer, lung cancer, or glioblastoma in a patient, wherein said cancer is associated with dysregulation of the HGF/c-MET signaling pathway, comprising administering to said patient a therapeutically effective amount of a compound, selected from
   2-chloro-N-[(1S)-1-(5-methyl-1,2,4-oxadiazol-3-yl) ethyl]-4-[7-(quinolin-6-ylmethyl)imidazo[1,2-b][1,2, 4]triazin-2-yl]benzamide;
   or a pharmaceutically acceptable salt of any of the aforementioned.

2. A method of treating gastric cancer, cancer of the kidney, liver cancer, lung cancer, or glioblastoma in a patient comprising administering to said patient a therapeutically effective amount of a compound selected from
   2-chloro-N-[(1S)-1-(5-methyl-1,2,4-oxadiazol-3-yl) ethyl]-4-[7-(quinolin-6-ylmethyl)imidazo[1,2-b][1,2, 4]triazin-2-yl]benzamide;
   or a pharmaceutically acceptable salt of any of the aforementioned.

3. The method of claim 1, wherein said cancer is gastric cancer.

4. The method of claim 1, wherein said cancer is cancer of the kidney.

5. The method of claim 1, wherein said cancer is liver cancer.

6. The method of claim 1, wherein said cancer is lung cancer.

7. The method of claim 1, wherein said cancer is glioblastoma.

8. The method of claim 2, wherein said cancer is gastric cancer.

9. The method of claim 2, wherein said cancer is cancer of the kidney.

10. The method of claim 2, wherein said cancer is liver cancer.

11. The method of claim 2, wherein said cancer is lung cancer.

12. The method of claim 2, wherein said cancer is glioblastoma.

* * * * *